United States Patent [19]

Wang et al.

[11] 4,299,828

[45] Nov. 10, 1981

[54] CORTICOSTEROID STICK FORMULATIONS

[75] Inventors: Yu-chang J. Wang; Thomas M. Wong, both of North Brunswick, N.J.

[73] Assignee: E. R. Squibb & Sons, Inc., Princeton, N.J.

[21] Appl. No.: 197,711

[22] Filed: Oct. 16, 1980

Related U.S. Application Data

[63] Continuation of Ser. No. 44,293, May 31, 1979, abandoned.

[51] Int. Cl.³ .................... A61K 31/56; A01N 45/00
[52] U.S. Cl. .................................. 424/238; 424/243
[58] Field of Search .............................. 424/238, 243

[56] References Cited

U.S. PATENT DOCUMENTS 3,980,778  9/1976  Ayer et al. .............. 260/397.45
4,048,309  9/1977  Chen et al. .............. 260/397.45
4,048,310  9/1977  Chen et al. .............. 260/397.45

*Primary Examiner*—Elbert L. Roberts
*Attorney, Agent, or Firm*—Lawrence S. Levinson; Burton Rodney

[57] ABSTRACT

Corticosteroid formulations in the form of a lipophilic stick are provided which are used as anti-inflammatory agents; the lipophilic stick includes the corticosteroid, such as halcinonide or triamcinolone acetonide, dissolved in an oleaginous solvent which is miscible with the other stick ingredients, which solvents include isostearyl alcohol, dibutyl sebacate, castor oil and/or mineral oil, one or more waxes to provide body and stiffness, and an anti-microbial agent to prevent growth and eliminate the spreading of microbes on the surface of the stick, such as propylene glycol or 1,3-butylene glycol.

14 Claims, No Drawings

CORTICOSTEROID STICK FORMULATIONS

This application is a continuation of application Ser. No. 44,293, filed May 31, 1979, now abandoned.

DESCRIPTION OF THE INVENTION

The present invention relates to corticosteroid formulations in the form of a stick which include a corticosteroid fully dissolved in an oleaginous solvent and an anti-microbial compound which prevents growth of microbes on the stick surface and their spreading from one area of application to another.

Topical corticosteroid formulations are extensively employed in the treatment of skin disorders, such as dermatitis. To be therapeutically effective, the active ingredient should be in a molecular dispersion to facilitate desired percutaneous absorption which is particularly important in achieving a therapeutic response for the management of psoriasis.

Conventional dosage forms such as ointment, creams, lotions and the like, used to apply potent steroid to the skin require the patient to use his fingers. Such exposure of the fingers to the steroid could be undesirable. Moreover, a large percentage of dermatoses patients are senile or institutionalized, and many of them require a second party to apply the steroid to affected areas.

A particularly convenient formulation which overcomes the above difficulties is the stick. Use of a stick formulation does not expose fingers to potent steroids and thus may also eliminate possible eye contamination, is ideal for second party application, may be indexed directly to the affected site, covers large areas with relative ease, and all without accumulation of waste.

Various steroid formulations in the form of a stick are disclosed in U.S. Pat. Nos. 4,048,309 and 4,082,881.

It has been found that during application, the stick comes in direct contact with diseased skin and may pick up some microbes. In order to prevent the growth and spread of such microbes, it has been suggested to employ in stick formulations preservatives normally useful in creams or lotions, such as the parabens, chlorocresol, benzoic acid, and chlorobutanol. Unfortunately, however, these cream or lotion preservatives have been found to be virtually ineffective in stick formulations.

In accordance with the present invention, to prevent the growth of these microbes on the stick surface and also to eliminate their spread from one area of application to another, an anti-microbial compound which is effective in stick formulations, even in the presence of oleaginous solvents, is included.

The stick formulation of the present invention comprises two systems, namely, (a) oleaginous solvents to dissolve corticosteroids, and (b) waxes to provide body and stiffness to the formulation, together with an anti-microbial compound which will be effective in sticks which are primarily oleaginous, and optionally liquid softeners or emollients, antioxidants, and/or opacifying agents.

Surprisingly and unexpectedly, it has been found that propylene glycol and 1,3-butylene glycol which are immiscible with oleaginous solvents are particularly effective in the stick formulations of the invention for preventing growth and spread of microbes.

Unlike most of the conventional topical products in which corticosteroids are in solid dispersion, corticosteroids in stick formulations are all solubilized assuring maximal possible bioavailability. Solvents suitable for use herein have to be miscible among themselves and with the waxes at the concentration employed so as to prevent separation and syneresis.

The amount of solvent employed preferably should be just sufficient to dissolve all the corticosteroid used in the formulation, that is, ideally, the concentration of dissolved steroid should result in a saturated solution. Should the solution be oversaturated, some of the steroid will undesirably crystallize out. If the solution is undersaturated, the extra solvent will increase the affinity of the base (waxes) for the steroid and will therefore slow the steroid release rate.

In addition, the solvents employed herein shall have low intrinsic viscosity, so that after wax matrices are broken down during application, the solvent can readily penetrate the skin. For this reason, where castor oil or mineral oil is employed, these solvents preferably are diluted with dibutyl sebacate or diisopropyl sebacate to reduce their intrinsic viscosities.

Accordingly, as will be seen hereinafter, in order to achieve the necessary saturated solution, while employing a solvent having low intrinsic viscosity, a co-solvent may be employed with the major oleaginous solvent for the steroid. The steroid component will usually be less soluble in the co-solvent and in this manner a solvent system is fashioned which is of low intrinsic viscosity and produces the properly balanced saturated solution. Examples of oleaginous solvents which may be employed herein include, but are not limited to, castor oil, mineral oil, isostearyl alcohol, isopropyl palmitate, isopropyl myristate, dibutyl sebacate, diisopropyl sebacate and mixtures thereof depending upon the solubility of the steroid of choice in the solvent and the intrinsic viscosity of the solvent. Thus, for example, castor oil is a good oleaginous solvent for halcinonide; to complete the solvent system, the castor oil will be balanced with isostearyl alcohol, which is not as good a solvent for halcinonide as is castor oil. In this manner, a solvent mixture which has a desirable solubility, for example, 100 mg halcinonide in 60 gm of the solvent mixture, is achieved. When such a steroid-solvent mixture is formulated with waxes and an anti-microbial compund into a stick of 100 gm, a 0.1% halcinonide product is formed.

Other useful mixtures are isostearyl alcohol and dibutyl or diisopropyl sebacate, and castor oil and dibutyl or diisopropyl sebacate which are miscible with all waxes at desired concentrations. However, castor oil and mineral oil are immiscible and thus this combination should be avoided.

Generally, the mixture of oleaginous solvents will be employed in an amount within the range of from about 45 to about 85% by weight, and preferably from about 50 to about 80% by weight of the stick formulation. In particularly preferred embodiments depending upon the steroid to be present, isostearyl alcohol is employed in a weight ratio to castor oil within the range of from about 3:1 to about 0.8:1 and preferably from about 2.5:1 to about 1:1, isostearyl alcohol is employed in a weight ratio to dibutyl sebacate within the range of from about 0.5:1 to about 2:1 and preferably from about 0.8:1 to about 1.5:1, and castor oil is employed in a weight ratio to dibutyl sebacate within the range of from about 0.5:1 to about 1.5:1 and preferably from about 0.8:1 to about 1.2:1.

The selection of waxes for use herein is important to optimize the stick formulation. Thus, in preferred embodiments, waxes of a wide range of melting point are used to avoid a grainy appearance in the stick. It is also prferably that waxes have minimal solubility in oleaginous solvents so that gel structure will form readily and intrinsic viscosity will not increase substantially. Waxes having some emulsifying activity, such as glyceryl monostearate reduce interfacial tension between moist skin and the oleaginous solvent and are used for this reason. Examples of other waxes suitable for use herein include high melting waxes, such as carnauba wax, white wax, ozokerite, beeswax, candelilla wax, cetyl alcohol, petrolatum, mineral oil thickened with polyethylene as disclosed in U.S. Pat. Nos. 2,627,938, 2,628,187, 2,628,205 and 3,733,403, and various mixtures thereof.

The waxes will normally be present in an amount within the range of from about 10 to about 40% and preferably from about 15 to about 30% by weight of the stick formulation.

The anti-microbial compounds employed in the stick formulations of the invention may be present in an amount within the range of from about 1 to about 25% and preferably from about 2 to about 10% by weight, and optimally from about 3 to about 8% by weight of the entire stick formulation. Examples of anti-microbial agents suitable for use herein include propylene glycol, 1,3-butylene glycol, and mixtures thereof. Propylene glycol or 1,3-butylene glycol present in the stick formulation of the invention at a concentration of 1-3% or higher kills bacteria, while at a concentration of 6% or higher kills 99.9% of the bacteria originally present on the stick. The glycols not only serve as anti-microbial agents but also as a penetration enhancer.

The fact that the above anti-microbial agents can be effectively included in the stick formulations of the invention is indeed surprising inasmuch as these anti-microbial agents are generally immiscible with the oleaginous materials necessary in the stick formulations. However, it has been found that where the amounts of anti-microbial agent specified above are employed, the anti-microbial agent remains homogeneously dispersed (and not dissolved) in the stick without separating therefrom.

The active steroid ingredient employed in the formulations of the invention will preferably comprise a steroid which will be present in an amount of from about 0.001 to about 3% by weight, and preferably from about 0.025 to about 0.2% based on the total weight of the composition, depending upon the type of steroid employed and its solubility in the oleaginous solvent vehicle.

Exemplary of the steroids contemplated are the acetonide derivatives of steroids of the pregnane series described in U.S. Pat. Nos. 3,048,581 and 3,937,720. Included within the steroids described by the former patent are triamcinolone acetonide and halcinonide. In addition, the stick formulation of the invention may include steroids disclosed in U.S. Pat. Nos. 3,976,637, 3,979,417, 3,994,935, 4,018,757, 4,116,978, 4,018,774, 4,091,036, 4,094,840, 4,133,811 and 4,146,538 and U.S. application Ser. No. 919,006, filed June 26, 1978, now U.S. Pat. No. 4,160,772 and U.S. application Ser. No. 919,020, filed June 26, 1978, now U.S. Pat. No. 4,164,504. It is emphasized that these steroids are meant to be exemplary only and it is not meant to limit this invention to use with any particular steroid or group of topically active anti-inflammatory steroids.

The steroid stick formulation of the invention may also optionally include an opacifying agent, such as titanium dioxide, serving as indicator for homogeneity of dispersion, in an amount within the range of from about 0.2 to about 1% and preferably from about 0.3 to about 0.8% by weight based on the entire formulation. An antioxidant may also optionally be included in an amount within the range of from about 0.005 to about 0.1% and preferably from about 0.01 to about 0.03% by weight based on the entire formulation.

Examples of preferred steroid stick formulations in accordance with the present invention include, but are not limited to, the following:

|  | Ranges |
|---|---|
| Halcinonide Stick, 0.025% | |
| Halcinonide, micronized | 0.020–0.03 gm. |
| Isostearyl alcohol | 30–45 gm. |
| Castor oil | 15–35 gm. |
| Propylene glycol or 1,3-butylene glycol | 6–25 gm. |
| White wax | 2–6 gm. |
| Ozokerite | 3–7 gm. |
| Candelilla wax | 1–3 gm. |
| Carnauba wax | 2–4 gm. |
| Glyceryl stearate | 2–4 gm. |
| Cetyl alcohol | 5–9 gm. |
| Halcinonide Stick, 0.1% | |
| Halcinonide, micronized | 0.09–0.11 gm. |
| Isostearyl alcohol | 30–45 gm. |
| Castor oil | 15–35 gm. |
| Propylene glycol or 1,3 butylene glycol | 6–25 gm. |
| White wax | 2–6 gm. |
| Ozokerite | 3–7 gm. |
| Candelilla wax | 1–3 gm. |
| Carnauba wax | 2–4 gm. |
| Glyceryl stearate | 2–4 gm. |
| Cetyl alcohol | 5–9 gm. |
| Kenalog Stick, 0.025% | |
| Triamcinolone acetonide, micronized | 0.02–0.03 gm. |
| Isostearyl alcohol | 30–45 gm. |
| Castor oil | 15–35 gm. |
| Propylene glycol or 1,3-butylene glycol | 6–25 gm. |
| White wax | 2–6 gm. |
| Ozokerite | 3–7 gm. |
| Candelilla wax | 1–3 gm. |
| Carnauba wax | 2–4 gm. |
| Glyceryl stearate | 2–4 gm. |
| Cetyl alcohol | 5–9 gm. |
| Kenalog Stick, 0.1% | |
| Triamcinolone acetonide, micronized | 0.09–0.11 gm. |
| Isostearyl alcohol | 30–45 gm. |
| Castor oil | 15–35 gm. |
| Propylene glycol or 1,3-butylene glycol | 6–25 gm. |
| White wax | 2–6 gm. |
| Ozokerite | 3–7 gm. |
| Candelilla wax | 1–3 gm. |
| Carnauba wax | 2–4 gm. |
| Glyceryl stearate | 2–4 gm. |
| Cetyl alcohol | 5–9 gm. |

Other Steroid Stick Formulations Containing 0.1% Steroid A or B

<u>A</u>   21-(Acetyloxy)-9-fluoro-1', 2', 3', 4'-tetrahydroo-11β-hydroxypregna-1,4-dieno[16α,17-b]naphthalene-3, 20-dione or <u>B</u>   21-Chloro-9-fluoro-1', 2', 3', 4'-tetrahydro-11β-hydroxypregna-1, 4-dieno[16α,17-b]naphthalene-3, 20-dione

|  | Steroid Stick A | Steroid Stick B |
|---|---|---|
| Isostearyl alcohol | 30–40 gm | — |
| Castor oil | — | 30–40 gm |
| Dibutyl sebacate | 30–40 gm | 30–40 gm |
| Propylene glycol or 1,3- | | |

| | -continued | |
|---|---|---|
| butylene glycol | 5-10 gm | 5-10 gm |
| White wax | 1-5 gm | 1-5 gm |
| Ozokerite | 2-6 gm | 2-6 gm |
| Candelilla wax | 1-5 gm | 1-5 gm |
| Carnauba wax | 4-6 gm | 4-6 gm |
| Glyceryl stearate | 3-5 gm | 3-5 gm |
| Cetyl alcohol | 1-8 gm | 1-8 gm |
| Steroid A | 0.09-0.11 gm | — |
| Steroid B | — | 0.09-0.11 gm |

The following Examples represent preferred embodiments of the present invention.

EXAMPLES 1 TO 11

A series of lipophilic sticks having formulations as shown in the following table are prepared as described below.

The steroid is dissolved in the oleaginous solvents, that is, isostearyl alcohol, castor oil, and dibutyl sebacate, where employed, with gentle heat not over 90° C. A molten mixture of the remaining ingredients is added to the above solution at 90° C. The mixture is poured into a mold and chilled to solidify the mixture to a stick.

| | Parts by Weight | | | | | | | | | | |
|---|---|---|---|---|---|---|---|---|---|---|---|
| Example No. | 1 | 2 | 3 | 4 | 5 | 6 | 7 | 8 | 9 | 10 | 11 |
| Isostearyl alcohol | 35 | 38 | 39 | 35 | 38 | 39 | 37 | 37 | 33 | — | — |
| Castor oil | 18 | 27 | 32 | 18 | 12 | 32 | — | — | — | 37 | 37 |
| Propylene glycol | 24 | 12 | 6 | — | — | — | 6 | — | — | 6 | — |
| Butylene glycol | — | — | — | 24 | 12 | 6 | — | 6 | 6 | — | 6 |
| Dibutyl sebacate | — | — | — | — | — | — | 37 | 37 | 33 | 37 | 37 |
| White Wax<br>Ozokerite<br>Candelilla wax<br>Glyceryl stearate<br>Cetyl alcohol | 23 | 23 | 23 | 23 | 23 | 23 | 20 | 20 | 28 | 22 | 20 |
| Halcinonide | 0.1 | 0.1 | 0.1 | 0.1 | 0.1 | 0.1 | — | — | — | — | — |
| Steroid A | — | — | — | — | — | — | 0.1 | 0.1 | 0.1 | — | — |
| Steroid B | — | — | — | — | — | — | — | — | — | 0.1 | 0.1 |

Steroid A - 21-(Acetyloxy)-9-fluoro-1',2',3',4'-tetrahydro-11β-hydroxypregna-1,4-dieno-8-16α,17-b]naphthalene-3,20-dione
Steroid B - 21-Chloro-9-fluoro-1',2',3',4'-tetrahydro-11βhydroxypregna-1,4-dieno[16α,17-b]naphthalene-3,20-dione The above lipophilic sticks in accordance with the invention contain the steroid component fully dissolved in the form of a saturated solution in each of the mixtures of oleaginous solvents shown, which solvent mixtures have low intrinsic viscosities. The above sticks are found to be therapeutically effective while the anti-microbial compounds present, namely, propylene glycol or 1,3-butylene glycol, are found to prevent the growth and spread of bacteria on the stick from one application area to another.

What is claimed is:

1. A method for preventing growth and spread of bacteria on a steroid stick composition from one application area to another, the steroid stick composition including an effective amount of an anti-inflammatory corticosteroid, one or more oleaginous solvents in which said corticosteroid is fully dissolved, and one or more waxes to impart body and stiffness, which method comprises including in the steroid stick composition 1,3-butylene glycol in an amount within the range of from about 1 to about 8% by weight of the steroid stick composition, said 1,3-butylene glycol being separate and apart from the oleaginous solvents.

2. The method as defined in claim 1 where in said stick said one or more oleaginous solvents are present in an amount within the range of from about 45 to about 85% by weight of the composition.

3. The method as defined in claim 1 wherein said oleaginous solvents include isostearyl alcohol, mineral oil, castor oil, dibutyl sedacate, diisopropyl sebacate or mixtures thereof.

4. The method as defined in claim 1 wherein said steroid is halcinonide, triamcinolone acetonide, 21-(acetyloxy)-9-fluoro-1',2',3',4'-tetrahydro-11β-hydroxy-pregna-1,4-dieno-[16α,17-b]naphthalene-3,20-dione or 21-chloro-9-fluoro-1',2',3',4'-tetrahydro-11β-hydroxy-pregna-1,4-dieno [16α,17-b]naphthalene-3,20-dione.

5. The method as defined in claim 1 wherein said anti-microbial agent is present in an amount of within the range of from about 2 to about 8% by weight of said stick formulation.

6. The method as defined in claim 1 wherein said anti-microbial agent is present in an amount of within the range of from about 3 to about 8% by weight of said stick formulation.

7. The method as defined in claim 1 wherein said steroid is present in an amount within the range of from about 0.005 to about 0.6% by weight of the composition.

8. The method as defined in claim 1 wherein said waxes are present in an amount within the range of from about 10 to about 40% by weight of the composition.

9. The method as defined in claim 1 wherein said steroid is halcinonide and said oleaginous solvent comprises a mixture of isostearyl alcohol and castor oil.

10. The method as defined in claim 1 wherein said steroid is triamcinolone acetonide, and said oleaginous solvent comprises castor oil and dibutyl sebacate.

11. The method as defined in claim 1 wherein said steroid is 21-(acetyloxy)-9-fluoro-1',2',3',4'-tetrahydro-11β-hydroxy-pregna-1,4-dieno[16α,17-b]naphthalene-3,20-dione and said oleaginous solvent comprises isostearyl alcohol and dibutyl sebacate.

12. The method as defined in claim 1 wherein said steroid is 21-chloro-9-fluoro-1',2',3',4'-tetrahydro-11β-hydroxypregna-1,4-dieno-[16α,17-b]naphthalene-3,20-dione and said oleaginous solvent is castor oil and dibutyl sebacate.

13. The method as defined in claim 1 wherein said waxes include white wax, ozokerite, candelilla wax, carnauba wax, glyceryl stearate, cetyl alcohol and mixtures thereof.

14. A method of treating dermatitis, which comprises administering topically an effective amount of a steroid stick composition as defined in claim 1.

* * * * *

UNITED STATES PATENT AND TRADEMARK OFFICE
CERTIFICATE OF CORRECTION

PATENT NO. : 4,299,828
DATED : November 10, 1981
INVENTOR(S) : Yu-chang J. Wang et al.

It is certified that error appears in the above–identified patent and that said Letters Patent are hereby corrected as shown below:

Column 2, line 42, "compund" should read --compound--.
Columns 5 and 6, in the table for Examples 1 to 11,
　Steroid A second occurrence, "8-16α" should read --[16α--;
　and Steroid B second occurrence, insert a hyphen after "11β".
Column 6, line 5, "sedacate" should read --sebacate--.

Signed and Sealed this

Twenty-third Day of March 1982

[SEAL]

Attest:

GERALD J. MOSSINGHOFF

Attesting Officer　Commissioner of Patents and Trademarks